(12) United States Patent
Miyake

(10) Patent No.: US 9,877,702 B2
(45) Date of Patent: Jan. 30, 2018

(54) ULTRASOUND OBSERVATION APPARATUS, ULTRASOUND OBSERVATION SYSTEM, AND ACTUATION METHOD FOR ULTRASOUND OBSERVATION APPARATUS

(71) Applicant: OLYMPUS CORPORATION, Tokyo (JP)

(72) Inventor: Tatsuya Miyake, Hino (JP)

(73) Assignee: OLYMPUS CORPORATION, Tokyo (JP)

( * ) Notice: Subject to any disclaimer, the term of this patent is extended or adjusted under 35 U.S.C. 154(b) by 0 days.

(21) Appl. No.: 14/989,929

(22) Filed: Jan. 7, 2016

(65) Prior Publication Data
US 2016/0113629 A1    Apr. 28, 2016

Related U.S. Application Data

(63) Continuation of application No. PCT/JP2015/057196, filed on Mar. 11, 2015.

(30) Foreign Application Priority Data

Aug. 25, 2014    (JP) .................................. 2014-170752

(51) Int. Cl.
| | |
|---|---|
| *A61B 8/00* | (2006.01) |
| *A61B 8/08* | (2006.01) |
| *A61B 8/12* | (2006.01) |

(52) U.S. Cl.
CPC ............. *A61B 8/5207* (2013.01); *A61B 8/08* (2013.01); *A61B 8/12* (2013.01); *A61B 8/4444* (2013.01); *A61B 8/461* (2013.01); *A61B 8/485* (2013.01)

(58) Field of Classification Search
None
See application file for complete search history.

(56) References Cited

U.S. PATENT DOCUMENTS

| | | | |
|---|---|---|---|
| 2007/0032726 A1* | 2/2007 | Osaka | A61B 5/0048 600/459 |
| 2010/0331694 A1* | 12/2010 | Waki | A61B 8/08 600/443 |

(Continued)

FOREIGN PATENT DOCUMENTS

| | | |
|---|---|---|
| EP | 1629777 A1 | 3/2006 |
| JP | 2005-118152 A | 5/2005 |

(Continued)

*Primary Examiner* — Jonathan Cwern
(74) *Attorney, Agent, or Firm* — Scully, Scott, Murphy & Presser, P.C.

(57) ABSTRACT

An ultrasound observation apparatus including a displacement calculating section that measures displacement of a subject based on an ultrasound signal, an elastic-image generating section that generates an elastic image based on the measured displacement, a memory section that stores generated one or more elastic images, a determination-region setting section that sets a proper-image determination region for proper image determination in the elastic image according to a size of an ROI, a characteristic calculating section that calculates a region characteristic of the proper-image determination region, and a proper-image determining section that determines based on the region characteristic whether the elastic image is a proper image.

12 Claims, 11 Drawing Sheets

(56) References Cited

U.S. PATENT DOCUMENTS

2012/0136248 A1* 5/2012 Kanayama ............... A61B 8/06
600/437
2012/0253195 A1* 10/2012 Inoue ....................... A61B 8/08
600/438
2013/0182926 A1* 7/2013 Lee ..................... G06K 9/00671
382/131

FOREIGN PATENT DOCUMENTS

| JP | 4455003 B2 | 4/2010 |
| JP | 2010-119630 A | 6/2010 |
| JP | 2012-213545 A | 11/2012 |
| WO | WO 2004/105615 A1 | 12/2004 |
| WO | WO 2011/010626 A1 | 1/2011 |

* cited by examiner

ULTRASOUND OBSERVATION APPARATUS, ULTRASOUND OBSERVATION SYSTEM, AND ACTUATION METHOD FOR ULTRASOUND OBSERVATION APPARATUS

CROSS REFERENCE TO RELATED APPLICATION

This application is a continuation application of PCT/JP2015/057196 filed on Mar. 11, 2015 and claims benefit of Japanese Application No. 2014-170752 filed in Japan on Aug. 25, 2014, the entire contents of which are incorporated herein by this reference.

BACKGROUND OF THE INVENTION

1. Field of the Invention

The present invention relates to an ultrasound observation apparatus, an ultrasound observation system, and an actuation method for the ultrasound observation apparatus for generating an image including an elastic image based on an ultrasound signal obtained by transmitting and receiving ultrasound.

2. Description of the Related Art

An ultrasound observation apparatus that generates, from a distortion amount of a biological tissue caused by an oppression force, an elastic image representing hardness or softness of the biological tissue has been put to practical use.

A series of images acquired in such an ultrasound observation apparatus are once stored in an image memory or the like. A user selects, out of the series of images stored in the image memory, a proper image as an image for calculating elasticity information and an image for medical record storage.

Incidentally, when the ultrasound observation apparatus is set in an elastic image observation mode, a region having a distortion amount is larger than a predetermined threshold in an image is sometimes colored and displayed. However, not all frame images are always colored. Therefore, when the user selects the proper image, the user has to search for the proper image not only in colored frame images but also uncolored frame images.

In order to cope with such a point, for example, International Publication No. 2011/010626 discloses a technique for automatically extracting a proper image based on an oppression state to an organism. References used for extraction in the publication are an average of displacement, an average of elasticity information, displacement of pressure, fluctuation in pressure in a beam line direction, and the like.

Japanese Patent Application Laid-Open Publication No. 2012-213545 discloses an ultrasound diagnostic apparatus that, in order to provide a high-quality three-dimensional elastic image, determines elastic volume data formed by a plurality of two-dimensional elastic image including a noise image as a noise volume and hides a three-dimensional elastic image by the elastic volume data determined as the noise volume.

Further, Japanese Patent Application Laid-Open Publication No. 2005-118152 describes a technique for, in order to provide a high-quality elastic image, evaluating, based on various data (pressure data, displacement frame data, and elastic frame data) used in a generation process of a distortion elastic image (elastic frame data), a value of performing image display concerning respective measurement points in a region of interest (ROI), distinguishing useless information and useful information, and finally not leaving (masking to hide) the useless information as an image.

SUMMARY OF THE INVENTION

An ultrasound observation apparatus according to an aspect of the present invention is an ultrasound observation apparatus that generates an ultrasound image based on an ultrasound signal generated from ultrasound transmitted to a subject and reflected, the ultrasound observation apparatus including: a transmitting section that transmits a driving signal for generating the ultrasound transmitted to the subject; a receiving section that receives the ultrasound signal generated from the ultrasound reflected by the subject; a displacement calculating section that measures displacement of the subject based on the ultrasound signal received by the receiving section; an elastic-image generating section that generates an elastic image based on the displacement measured by the displacement calculating section; a storing section that stores one or more of the elastic images generated by the elastic-image generating section; a determination-region setting section that sets, according to a size of an ROI, which is a region of interest, a proper-image determination region for determining a proper image out of the one or more elastic images stored in the storing section; a characteristic calculating section that calculates a region characteristic of the proper-image determination region; and a proper-image determining section that determines based on the region characteristic whether the elastic image in which the proper-image determination region is set is the proper image.

An ultrasound observation system according to an aspect of the present invention includes: the ultrasound observation apparatus; and an ultrasound probe that receives the driving signal transmitted from the transmitting section, transmits the ultrasound to the subject, receives the ultrasound reflected by the subject, generates the ultrasound signal, and transmits the ultrasound signal to the receiving section.

An actuation method for an ultrasound observation apparatus according to an aspect of the present invention is an actuation method for an ultrasound observation apparatus that generates an ultrasound image based on an ultrasound signal generated from ultrasound transmitted to a subject and reflected, the actuation method for the ultrasound observation apparatus including: a step in which a transmitting section transmits a driving signal for generating the ultrasound transmitted to the subject; a step in which a receiving section receives the ultrasound signal generated from the ultrasound reflected by the subject; a step in which a displacement calculating section measures displacement of the subject based on the ultrasound signal received by the receiving section; a step in which an elastic-image generating section generates an elastic image based on the displacement measured by the displacement calculating section; a step in which a storing section stores one or more of the elastic images generated by the elastic-image generating section; a step in which a determination-region setting section sets, according to a size of an ROI, which is a region of interest, a proper-image determination region for determining a proper image out of the one or more elastic images stored in the storing section; a step in which a characteristic calculating section calculates a region characteristic of the proper-image determination region; and a step in which a proper-image determining section determines based on the region characteristic whether the elastic image in which the proper-image determination region is set is the proper image.

DETAILED DESCRIPTION OF THE PREFERRED EMBODIMENTS

An embodiment of the present invention is explained below with reference to the drawings.

First Embodiment

Figure 1:
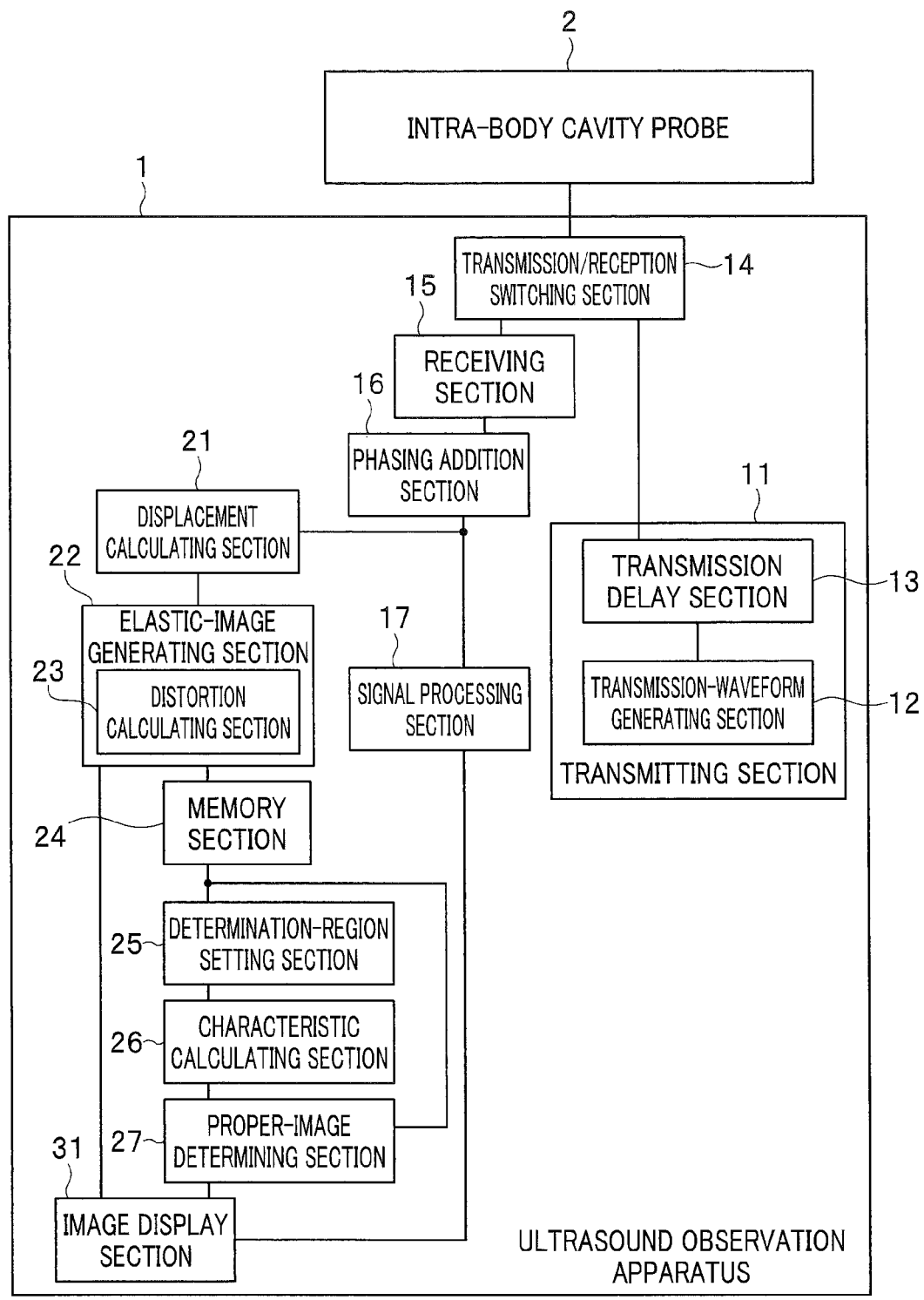
FIG. 1 is a block diagram showing a configuration of an ultrasound observation system in a first embodiment of the present invention.

FIG. 1 to FIG. 17 show a first embodiment of the present invention. FIG. 1 is a block diagram showing a configuration of an ultrasound observation system.

The ultrasound observation system includes an intra-body cavity probe 2 that transmits ultrasound to a subject and receives the ultrasound reflected by the subject and an ultrasound observation apparatus 1 that generates an ultrasound image based on an ultrasound signal obtained from the received ultrasound.

The intra-body cavity probe 2 is an ultrasound probe inserted into a body cavity and used. The intra-body cavity probe 2 includes an ultrasound transducer configured by arraying a large number of vibration elements, transmits ultrasound from an ultrasound transmission/reception surface of the ultrasound transducer to the subject, receives, on the ultrasound transmission/reception surface of the ultrasound transducer, the ultrasound reflected by the subject, and generates an ultrasound signal from the received ultrasound. Specifically, the intra-body cavity probe 2 is configured as an ultrasound probe of a convex type, an ultrasound probe of a radial type, or the like.

The ultrasound observation apparatus 1 includes a transmitting section 11, a transmission/reception switching section 14, a receiving section 15, a phasing addition section 16, a signal processing section 17, a displacement calculating section 21, an elastic-image generating section 22, a memory section 24, a determination-region setting section 25, a characteristic calculating section 26, a proper-image determining section 27, and an image display section 31.

The transmitting section 11 transmits a driving signal for generating ultrasound transmitted to a subject. The transmitting section 11 includes a transmission-waveform generating section 12 and a transmission delay section 13.

The transmission-waveform generating section 12 generates a signal waveform for driving the respective vibration elements configuring the ultrasound transducer and outputs the signal waveform as a driving signal.

The transmission delay section 13 delays the driving signal generated by the transmission-waveform generating section 12 to thereby adjust driving timing of the respective vibration elements configuring the ultrasound transducer. Consequently, a focus and a direction of an ultrasound beam transmitted from the ultrasound transducer are controlled. The ultrasound can be converged in a desired position (depth).

The transmission/reception switching section 14 includes, for example, a multiplexer that sequentially selects a plurality of vibration elements for performing transmission and reception of the ultrasound. The transmission/reception switching section 14 transmits the driving signal, which is transmitted from the transmitting section 11, to the ultrasound transducer and transmits an ultrasound signal (an echo signal), which is transmitted from the ultrasound transducer, to the receiving section 15.

The receiving section 15 receives the ultrasound signal, which is transmitted from the transmission/reception switching section 14, and performs processing such as amplification and conversion into a digital signal.

The phasing addition section 16 delays the ultrasound signal and adjusts a phase and then adds the ultrasound.

The signal processing section 17 performs coordinate conversion and interpolation processing on the ultrasound signal transmitted from the phasing addition section 16 and creates an ultrasound image as an image for display.

The displacement calculating section 21 measures displacement of the subject based on the ultrasound signal transmitted from the phasing addition section 16.

The elastic-image generating section 22 includes a distortion calculating section 23. The distortion calculating section 23 calculates, based on the displacement measured by the displacement calculating section 21, a distortion amount of a region of interest (ROI) (see an ROI 34 in FIG. 2 to FIG. 12) for elastic image display. The elastic-image generating section 22 calculates a modulus of elasticity of the subject based on the distortion amount calculated by the distortion calculating section 23. The elastic-image generating section 22 calculates a modulus of elasticity for each of coordinates of the subject. Therefore, a calculation result is an elastic image in which moduli of elasticity are distributed on a two-dimensional coordinate. The generation of the elastic image by the elastic-image generating section 22 is performed, for example, every frame. One or more elastic images are generated. The elastic-image generating section 22 further calculates a distortion amount of the ROI 34 based on the displacement measured by the displacement calculating section 21 and performs coloring on pixels of the elastic images in which the distortion amount is equal to or larger than a predetermined value.

The memory section 24 is a storing section that temporarily stores the one or more elastic images generated by the elastic-image generating section 22.

The determination-region setting section 25 sets, according to a size of the ROI 34, a proper-image determination region 37 (see FIG. 4 to FIG. 12, etc.) for determining a proper image out of the one or more elastic images stored in the memory section 24.

The characteristic calculating section 26 calculates a region characteristic of the proper-image determination region 37 set by the determination-region setting section 25. Specifically, the characteristic calculating section 26 calculates, as the region characteristic, for example, at least one of an average of the displacement of the proper-image determination region 37 measured by the displacement calculating section 21, dispersion of the displacement, a deviation of the displacement and an average of elasticity information of the proper-image determination region 37 calculated by the elastic-image generating section 22, dispersion of the elasticity information, and a deviation of the elasticity information. The characteristic calculating section 26 may calculate, as the region characteristic, at least one of the number of colored pixels and a total area of the colored pixels of the proper-image determination region 37, a ratio of the number of colored pixels to the number of pixels of the entire proper-image determination region 37, and a ratio of a total area of the colored pixels to an area of the entire proper-image determination region 37.

Note that a pressure detecting section for detecting pressure on an ultrasound transmission/reception surface for transmitting and receiving ultrasound may be further provided in the intra-body cavity probe 2, which is an ultrasound probe. The characteristic calculating section 26 may calculate, as the region characteristic, at least one of an average of pressure, a rate of change of the pressure, dispersion of the pressure, and a deviation of the pressure of the proper-image determination region 37 obtained based on a detection result of the pressure detecting section.

The proper-image determining section 27 determines based on the region characteristic calculated by the characteristic calculating section 26 whether the proper-image determination region 37 is a proper region. Further, when the proper-image determination region 37 is not the proper region, the proper-image determining section 27 causes the determination-region setting section 25 to set the proper-image determination region 37 again according to necessity. In this way, when at least one of the proper-image determination regions 37 set in the ROI 34 of the elastic image is the proper region, the proper-image determining section 27 determines that the elastic image in which the proper-image determination region 37 is set is a proper image.

The image display section 31 includes a display device such as a monitor and displays an image for display transmitted from the signal processing section 17. That is, in an ultrasound diagnosis mode, the image display section 31 displays an ultrasound image. In an elastic image observation mode, the image display section 31 displays an elastic image transmitted from the elastic-image generating section 22 or superimposes and displays the elastic image on the ultrasound image. When displaying the elastic image, the image display section 31 further superimposes and displays the proper-image determination region 37 transmitted from the proper-image determining section 27 on the elastic image according to necessity.

Figure 2:
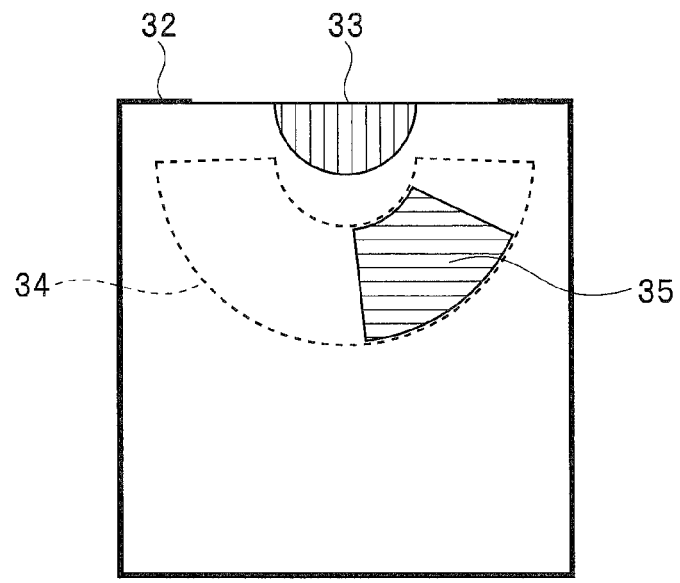
FIG. 2 is a diagram showing a state in which a region where a distortion amount in an ROI is equal to or larger than a predetermined value is displayed in the first embodiment.
Figure 3:
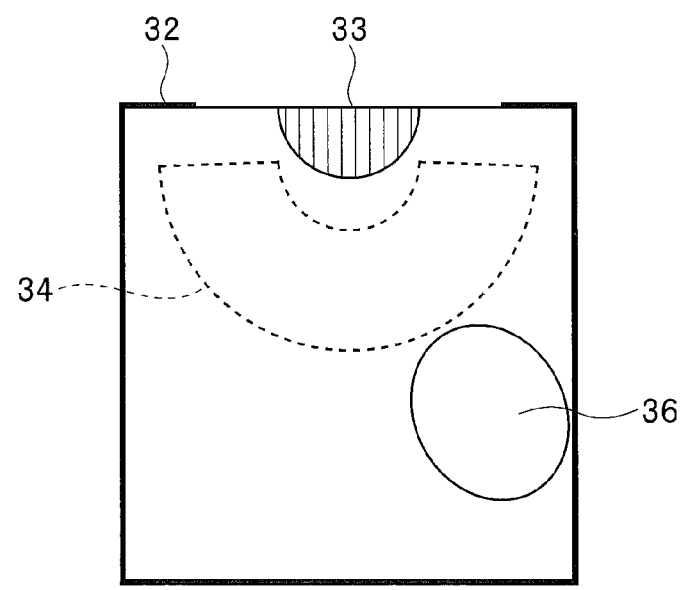
FIG. 3 is a diagram showing an example of a position of a displacement source with respect to the ROI in the first embodiment.

FIG. 2 is a diagram showing a state in which a region where a distortion amount is equal to or larger than a predetermined value in the ROI 34 is displayed. FIG. 3 is a diagram showing an example of a position of a displacement source with respect to the ROI 34.

As shown in the figure, on a screen 32 of the image display section 31, a probe image 33 showing a position of the intra-body cavity probe 2 itself as an image and the ROI 34 for elastic image display are displayed. A probe curvature radius R of the intra-body cavity probe 2 shown as the probe image 33 in FIG. 2 is, for example, 10 mm or less. The curvature radius R is relatively small. Further, a center angle of the ROI 34 is, for example, approximately 180°.

In this case, in the ROI 34, a region 35 formed by pixels having a distortion amount equal to or larger than the predetermined value is displayed, for example, as shown in FIG. 2. The region 35 is generated as, for example, an image colored in a specific color by the elastic-image generating section 22, is displayed on the image display section 31, and can be easily distinguished from other portions. Therefore, in the example shown in FIG. 2, a colored region and an uncolored region are present in the ROI 34 of the elastic image.

When the user determines, viewing such an image, whether the image is an image suitable for a diagnosis and storage of the image, since the image is only partially colored with respect to the entire ROI 34, it is assumed that the user sometimes determines that the image is not the proper image.

However, when an ultrasound probe is the intra-body cavity probe 2 inserted into a body cavity and used, in order to generate an elastic image, displacement of an organism due to a beat or a pulsation is used. For example, when a displacement source 36 such as a pulsation source or a beat source is present in the position shown in FIG. 3, only the region 35 shown in FIG. 2 receives proper pressure and has a distortion amount equal to or larger than the predetermined value in the ROI 34. A distortion amount equal to or larger than the predetermined value does not occur in other regions. In this way, when the curvature radius R of the intra-body cavity probe 2 is small or when the center angle of the ROI 34 is wide, it cannot be expected that the entire ROI 34 is colored.

Therefore, in this case, it should be determined that the image shown in FIG. 2 is a proper image. Therefore, in the present embodiment, as explained below, a region for determining that an image is a proper image is set according to the size of the ROI 34 for elastic image display, a region characteristic in the set region is calculated, and it is determined according to the calculated characteristic whether the image is the proper image.

Figure 13:
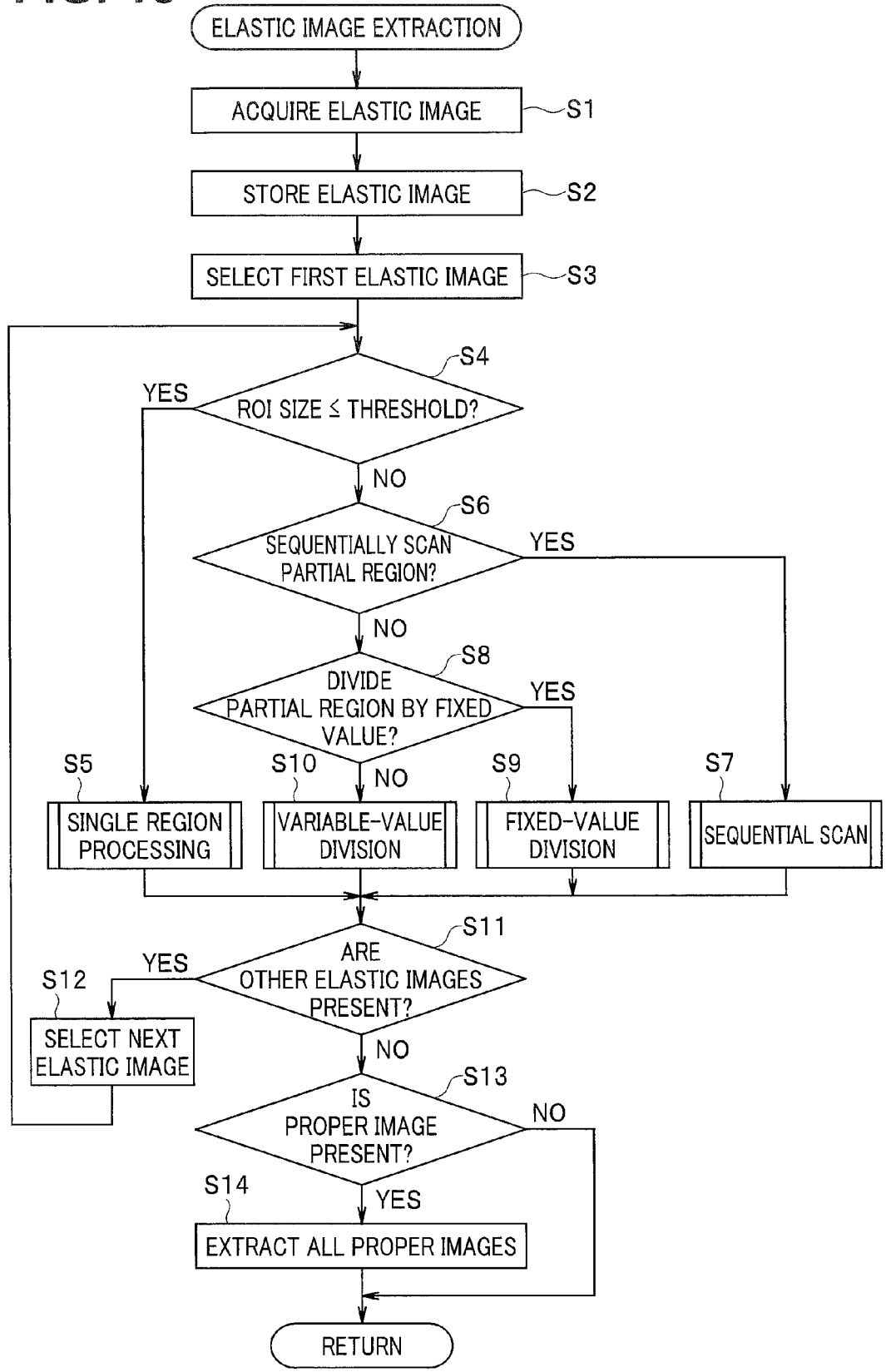
FIG. 13 is a flowchart showing elastic-image extraction processing in an ultrasound observation system of the first embodiment.

Action of generating an elastic image in such an ultrasound observation system is explained with reference to FIG. 13. FIG. 13 is a flowchart showing elastic image extraction processing in the ultrasound observation system.

When the ultrasound observation system is set in the elastic image observation mode while executing not-shown main processing, this elastic image extraction processing is started.

Then, first, the transmitting section 11 transmits an ultrasound signal to the intra-body cavity probe 2. Consequently, ultrasound is transmitted from the intra-body cavity probe 2 to the subject. The intra-body cavity probe 2 receives the ultrasound reflected by the subject, generates an ultrasound signal (an echo signal), and transmits the ultrasound signal to the ultrasound observation apparatus.

In the ultrasound observation apparatus, the receiving section 15 receives the ultrasound signal (the echo signal) via the transmission/reception switching section 14, the phasing addition section 16 and the displacement calculating section 21 perform processing, thereafter, the distortion calculating section 23 calculates a distortion amount of the ROI 34 for each of coordinate positions, and the elastic-image generating section 22 generates an elastic image based on the calculated distortion amount. Such acquisition of the elastic image is performed, for example, in frame units. Consequently, the ultrasound observation apparatus acquires one or more elastic images (step S1).

The ultrasound observation apparatus stores the one or more elastic images acquired in this way in the memory section 24 (step S2).

Thereafter, the ultrasound observation apparatus selects a first elastic image out of the elastic images stored in the memory section 24 (step S3).

Then, the determination-region setting section 25 determines whether a size of the ROI 34 of the selected elastic image (the size of the ROI 34 can be set by, for example, the user and, when the user setting is not performed, is set to a predetermined size) is equal to or smaller than a predetermined threshold (step S4). For example, a center angle of the ROI 34 is determined as the size of the ROI 34. The determination-region setting section 25 determines whether the center angle of the ROI 34 is equal to or smaller than a threshold. Note that the threshold used for the determination is desirably appropriately decided according to, for example, a size of the displacement source 36.

Figure 4:
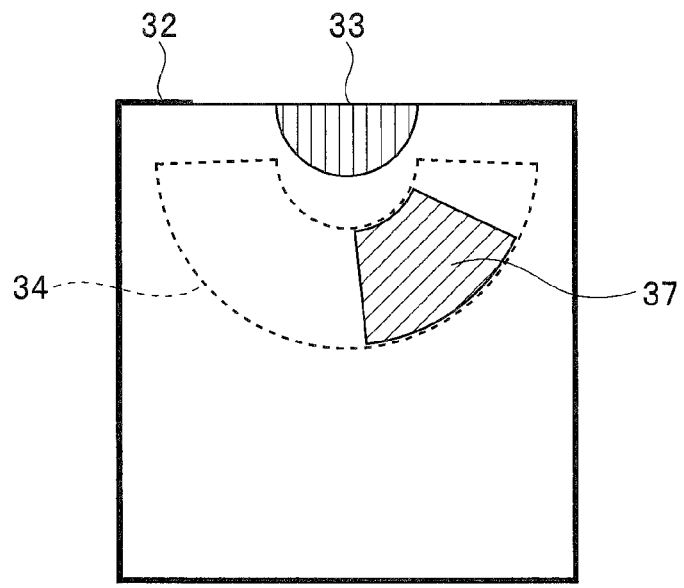
FIG. 4 is a diagram showing an example of a proper-image determination region set when a center angle of the ROI is larger than a predetermined threshold in the first embodiment.
Figure 5:
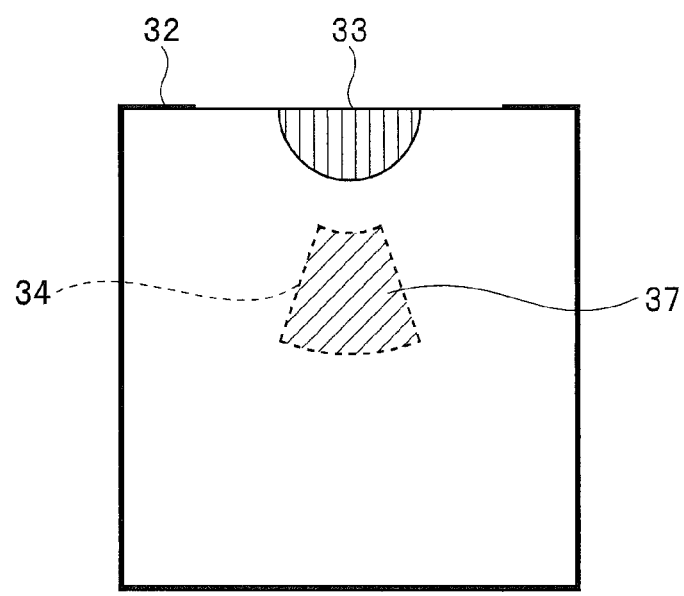
FIG. 5 is a diagram showing an example of a proper-image determination region set when the center angle of the ROI is equal to or smaller than the predetermined threshold.

FIG. 4 is a diagram showing an example of the proper-image determination region 37 set when the center angle of the ROI 34 is larger than the predetermined threshold. FIG. 5 is a diagram showing an example of the proper-image determination region 37 set when the center angle of the ROI 34 is equal to or smaller than the predetermined threshold.

As explained above, when the center angle of the ROI 34 is large, pressure from the displacement source 36 is not easily appropriately applied to the entire ROI 34. However, when the center angle is small, appropriate pressure is considered to be applied to the entire ROI 34.

Therefore, in a first case in which it is determined in step S4 that the center angle of the ROI 34 for elastic image display is equal to or smaller than the predetermined threshold, the ultrasound observation apparatus performs single region processing (step S5). As explained with reference to FIG. 14, the single region processing is processing for setting the entire ROI 34 as the proper-image determination region 37.

On the other hand, in a second case in which it is determined in step S4 that the center angle of the ROI 34 is larger than the predetermined threshold, as explained in step S7, step S9, or step S10, a partial region, which is a part in the ROI 34, is set as the proper-image determination region 37.

As a specific example, when the threshold is set to 60°, when the center angle of the ROI 34 is approximately 180° (i.e., larger than 60°) as shown in FIG. 4, only the partial region in the ROI 34 is set as the proper-image determination region 37 and, when the center angle of the ROI 34 is approximately 30° (i.e., 60° or less) as shown in FIG. 5, the entire ROI 34 is set as the proper-image determination region 37.

When it is determined in step S4 that the center angle of the ROI 34 is larger than the predetermined threshold, further, the ultrasound observation apparatus determines whether the partial region is set to be sequentially scanned (step S6).

When it is determined that the sequential scan is set, the ultrasound observation apparatus performs sequential scan processing (step S7). As explained below with reference to FIG. 15, the sequential scan processing is processing in which the determination-region setting section 25 sequentially moves the partial region from a reference position by an offset amount at a time such that the entire ROI 34 is covered with the partial regions in all moving positions and sets each of the partial regions in the respective moving positions as the proper-image determination region 37.

When it is determined in step S6 that the sequential scan is not set, the ultrasound observation apparatus determines whether fixed-value division of the partial region is set (step S8).

When it is determined that the fixed-value division is set, the ultrasound observation apparatus performs fixed-value division processing (step S9). As explained below with reference to FIG. 16, the fixed-value division processing is processing in which the determination-region setting section 25 divides the entire ROI 34 into a plurality of partial regions and sets each of the partial regions as the proper-image determination region 37 and is processing for setting the number of divisions into partial regions of the entire ROI 34 based on a fixed value.

On the other hand, when it is determined in step S8 that the fixed-value division is not set, the ultrasound observation apparatus performs variable-value division processing (step S10). As explained below with reference to FIG. 17, the variable-value division processing is processing in which the determination-region setting section 25 divides the entire ROI 34 into a plurality of partial regions and sets each of the partial regions as the proper-image determination region 37 and is processing for changing the number of divisions into the partial regions of the entire ROI 34 between a lower limit value and an upper limit value until the proper-image determination region 37 determined as the proper region by the proper-image determining section 27 is found.

When the processing in any one of step S5, step S7, step S9, or step S10 is performed in this way, the ultrasound observation apparatus determines whether unprocessed other elastic images are present in the memory section 24 (step S11).

When it is determined that other elastic images are present, the ultrasound observation apparatus selects a next elastic image out of the unprocessed elastic images (step S12). Then, the ultrasound observation apparatus shifts to step S4 and repeatedly performs the processing explained above.

When it is determined in step S11 that unprocessed elastic images are absent, the ultrasound observation apparatus determines based on a processing result in step S5, step S7, step S9, or step S10 whether proper images are present among elastic images stored in the memory section 24 (step S13).

When it is determined in step S13 that proper images are present, the ultrasound observation apparatus extracts and displays all of the proper images on, for example, the image display section 31 (step S14). When it is determined that proper images are absent, the ultrasound observation apparatus directly returns from the elastic image extraction processing to not-shown main processing.

Figure 14:
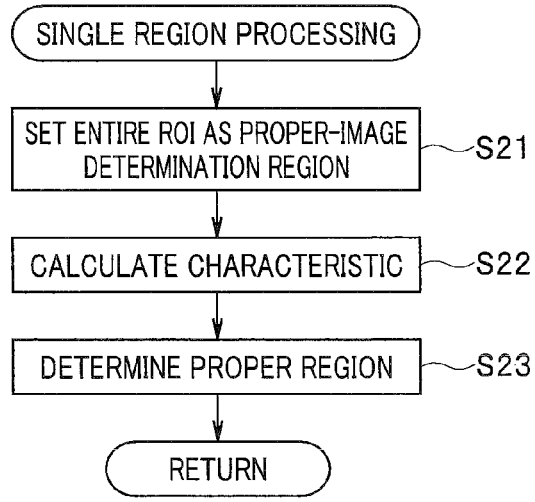
FIG. 14 is a flowchart showing single region processing in the first embodiment.

FIG. 14 is a flowchart showing single region processing.

When entering this processing in step S5 of FIG. 13, as explained above with reference to FIG. 5, the ultrasound observation apparatus sets the entire ROI 34 for elastic image display as the proper-image determination region 37 (step S21).

Subsequently, the ultrasound observation apparatus calculates a region characteristic of the proper-image determination region 37 (step S22). The ultrasound observation apparatus determines based on the calculated region characteristic whether the set proper-image determination region 37 is a proper region (step S23). The ultrasound observation apparatus returns from this processing to the processing shown in FIG. 13.

Figure 15:
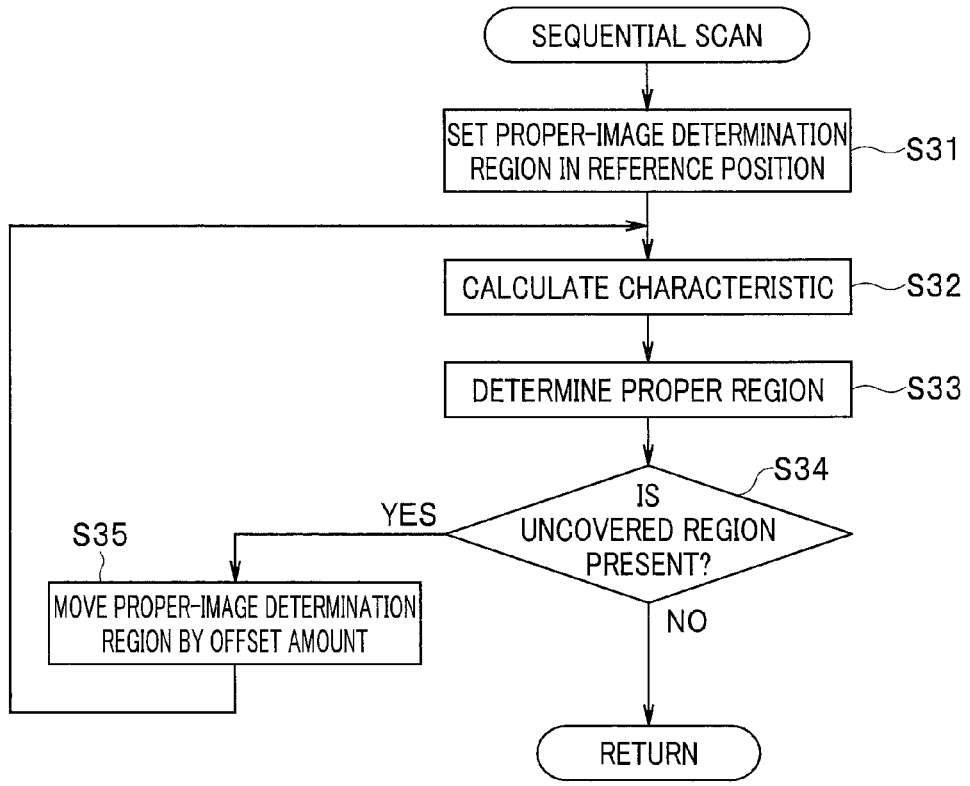
FIG. 15 is a flowchart showing sequential scan processing in the first embodiment.

FIG. 15 is a flowchart showing the sequential scan processing.

When entering this processing in step S7 of FIG. 13, first, the ultrasound observation apparatus sets the proper-image determination region 37 at a predetermined angle (e.g., 60° same as the angle set as the threshold in step S4) as a reference position in the ROI 34 for elastic image display (step S31).

Subsequently, the ultrasound observation apparatus calculates a region characteristic of the proper-image determination region 37 (step S32) and determines based on the calculated region characteristic whether the set proper-image determination region 37 is a proper region (step S33).

The ultrasound observation apparatus determines whether regions not determined as to whether the regions are the proper region are present in the ROI 34 (step S34). When it is determined that undetermined regions are present, the ultrasound observation apparatus moves the proper-image determination region 37 by a predetermined offset amount (e.g., an offset angle 30°) in the ROI 34 and sets a new proper-image determination region 37 (step S35). The ultrasound observation apparatus returns to step S32 and performs the processing explained above.

Figure 6:
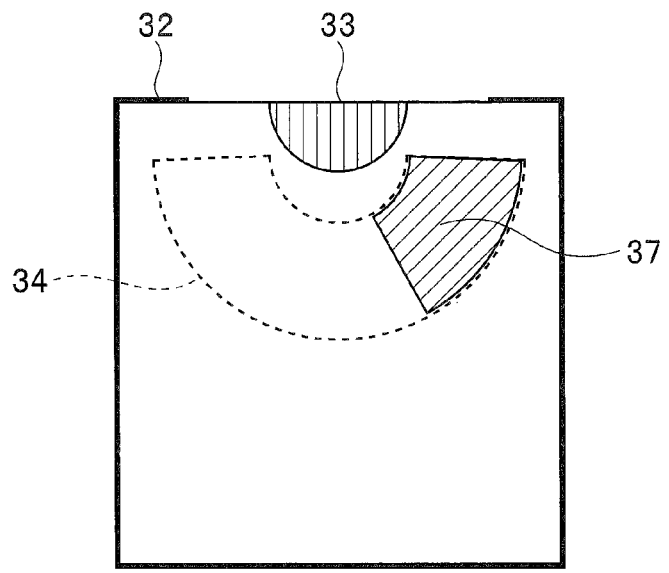
FIG. 6 is a diagram showing an example of a first position in sequentially scanning the proper-image determination region in the ROI of the first embodiment.
Figure 7:
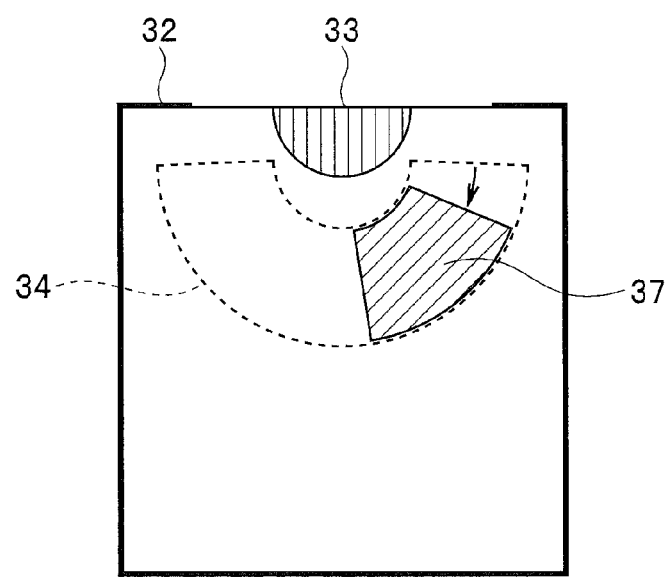
FIG. 7 is a diagram showing an example of a second position in sequentially scanning the proper-image determination region in the ROI of the first embodiment.
Figure 8:
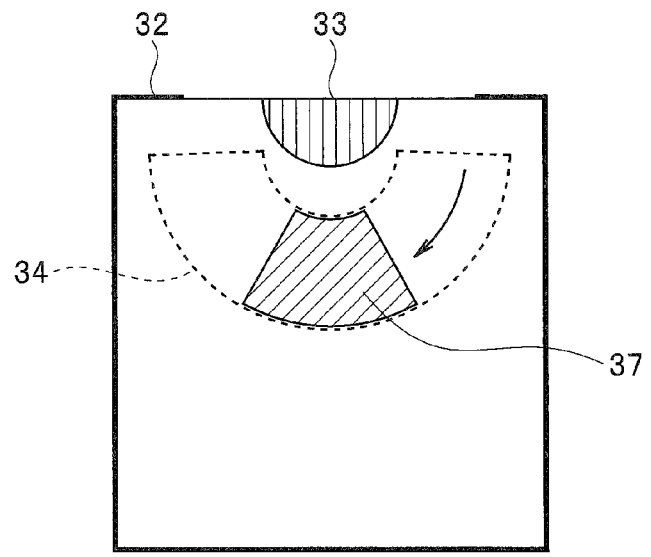
FIG. 8 is a diagram showing an example of a third position in sequentially scanning the proper-image determination region in the ROI of the first embodiment.

Consequently, as shown in FIGS. 6 to 8, the sequential scan in which the proper-image determination region 37 moves by, for example, 30° at a time in order in the ROI 34 is performed. FIG. 6 is a diagram showing an example of a first position in sequentially scanning the proper-image determination region 37 in the ROI 34. FIG. 7 is a diagram showing an example of a second position in sequentially scanning the proper-image determination region 37 in the ROI 34. FIG. 8 is a diagram showing an example of a third position in sequentially scanning the proper-image determination region 37 in the ROI 34.

When the scan from one end to the other end of the ROI 34 is carried out in this way and it is determined in step S34 that undetermined regions are absent, the ultrasound observation apparatus returns from this processing to the processing shown in FIG. 13.

Figure 16:
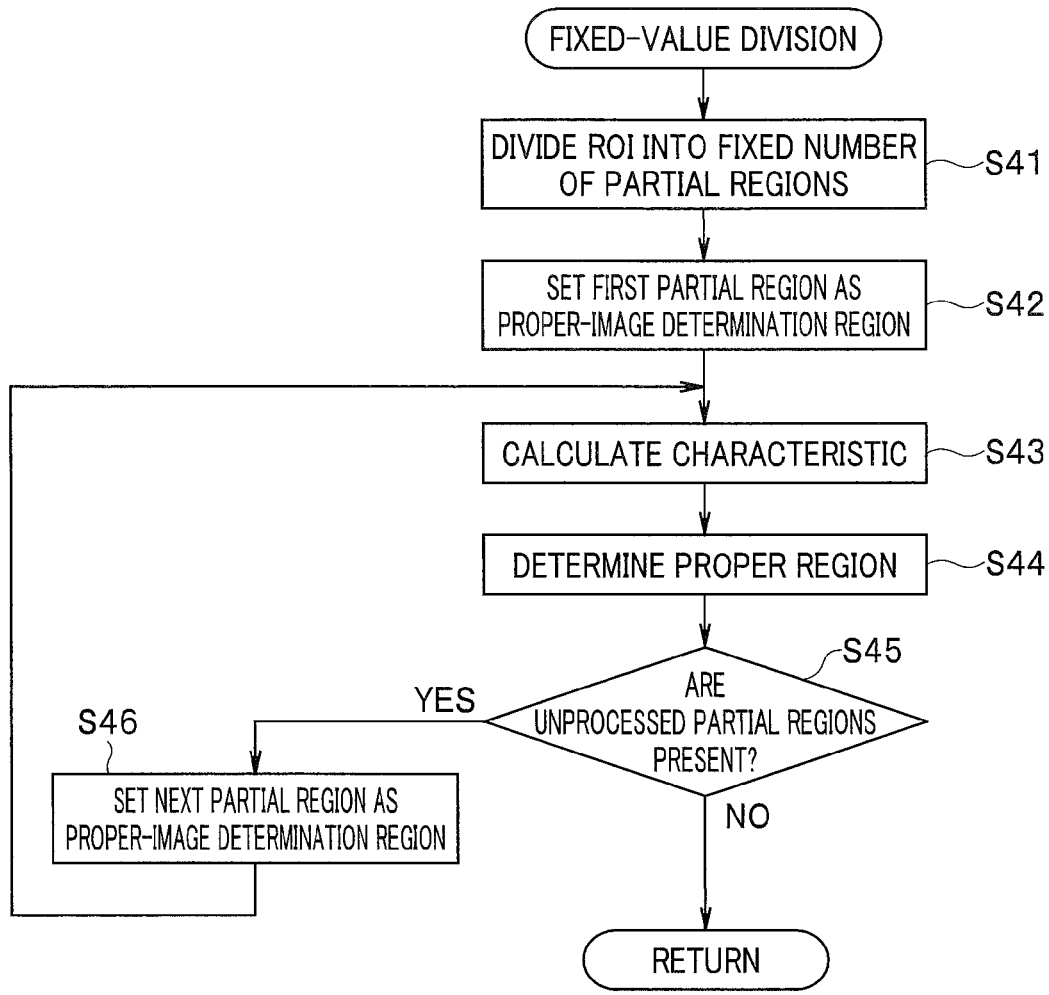
FIG. 16 is a flowchart showing fixed-value division processing in the first embodiment.

FIG. 16 is a flowchart showing the fixed-value division processing.

When entering this processing in step S9 in FIG. 13, first, the ultrasound observation apparatus divides the ROI 34 for elastic image display into partial regions based on a fixed value (step S41). The fixed value is, for example, a size of a partial region (an angle of the partial region) or the number of divisions.

Figure 9:
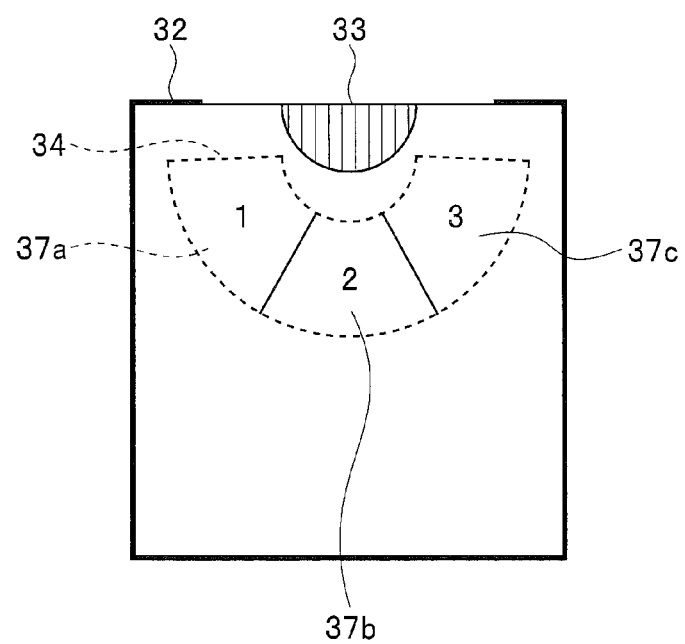
FIG. 9 is a diagram showing an example in which the proper-image determination region is divided by a fixed value in the ROI of the first embodiment.

For example, assuming that a center angle $\theta$ of the ROI 34 is larger than 60° (because, in the case of $\theta \le 60°$, the single region processing in step S5 is performed), the fixed value is set to an angle 60° of the partial region. In this case, when the center angle $\theta$ of the ROI 34 is, for example, 180°, as shown in FIG. 9, the entire ROI 34 is divided into three partial regions. The respective partial regions are set as first to third proper-image determination regions 37a to 37c in order. FIG. 9 is a diagram showing an example in which the proper-image determination region is divided by a fixed value in the ROI 34. In such a case in which the angle of the partial region is set to the fixed value, the number of divisions is different according to the center angle $\theta$ of the ROI 34 (e.g., when the center angle $\theta$ is 120°, the number of divisions is two).

When the fixed value is set to the number of divisions of three, as explained above, the ROI 34 is divided into three partial regions shown in FIG. 9 (as a desired division example, equally divided). In this case, the number of divisions is desirably given as a fixed value corresponding to a size of the center angle $\theta$ of the ROI 34. For example, when the center angle $\theta$ is $60° < \theta \le 120°$, the fixed value is set to two. When the center angle $\theta$ is $120° < \theta \le 180°$, the fixed value is set to three.

Subsequently, the ultrasound observation apparatus sets a first partial region among the divided partial regions as the proper-image determination region 37 (e.g., a first proper-image determination region 37a) (step S42), calculates a region characteristic of the proper-image determination region 37 (step S43), and determines based on the calculated region characteristic whether the set proper-image determination region 37 is a proper region (step S44).

The ultrasound observation apparatus determines whether unprocessed partial regions (partial regions not determined as to whether the partial regions are the proper region) are present (step S45). When it is determined that unprocessed partial regions are present, the ultrasound observation apparatus sets a next partial region as a new proper-image determination region 37 (step S46). The ultrasound observation apparatus returns to S43 and performs the processing explained above.

When it is determined in step S45 that unprocessed partial regions are absent in this way, the ultrasound observation apparatus returns from this processing to the processing shown in FIG. 13.

Figure 17:
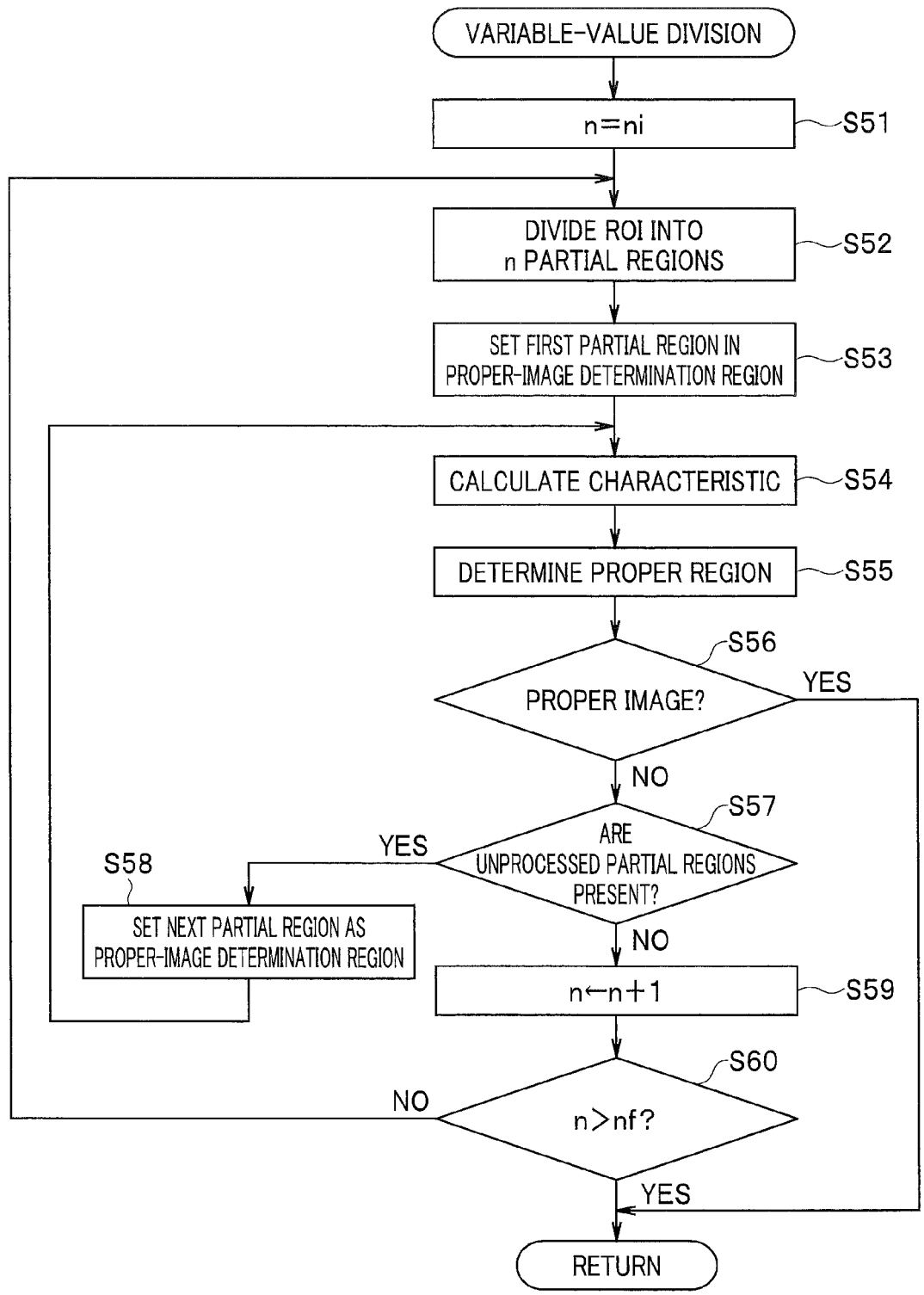
FIG. 17 is a flowchart showing variable-value division processing in the first embodiment.

FIG. 17 is a flowchart showing the variable-value division processing.

When entering this processing in step S10 in FIG. 13, first, the ultrasound observation apparatus sets, as an initial value, a lower limit value ni of the number of divisions in a variable n indicating the number of divisions (step S51). The lower limit value ni is, for example, 2 (when the number of divisions is one, the single region processing in step S5 is performed. Therefore, a suitable example of the lower limit value is 2 here).

Subsequently, the ultrasound observation apparatus divides (as a desirable division example, equally divides) the ROI 34 for elastic image display into n partial regions (step S52) and sets a first partial region among the divided partial regions in the proper-image determination region 37 (step S53).

Subsequently, the ultrasound observation apparatus calculates a region characteristic of the proper-image determination region 37 (step S54) and determines based on the calculated region characteristic whether the set proper-image determination region 37 is a proper region (step S55).

The ultrasound observation apparatus determines, according to whether it is determined in step S55 that the proper-image determination region 37 is the proper region, whether a processing target elastic image is a proper image (step S56).

When it is determined that the processing target elastic image is not a proper image, the ultrasound observation apparatus determines whether unprocessed partial regions (partial regions not determined as to whether the partial regions are a proper region) are present in the ROI 34 (step S57). When it is determined that unprocessed partial regions are present, the ultrasound observation apparatus sets the next partial region as a new proper-image determination region 37 (step S58). The ultrasound observation apparatus returns to step S54 and performs the processing explained above.

On the other hand, when it is determined in step S57 that unprocessed partial regions are absent, the ultrasound observation apparatus increases the variable n indicating the number of divisions by 1 (step S59) and then determines whether n is larger than an upper limit value nf of the number of divisions (step S60).

When it is determined that n is equal to or smaller than the upper limit value nf of the number of divisions, the ultrasound observation apparatus returns to step S52 and performs, as explained above, processing based on the number of divisions n set anew.

Figure 10:
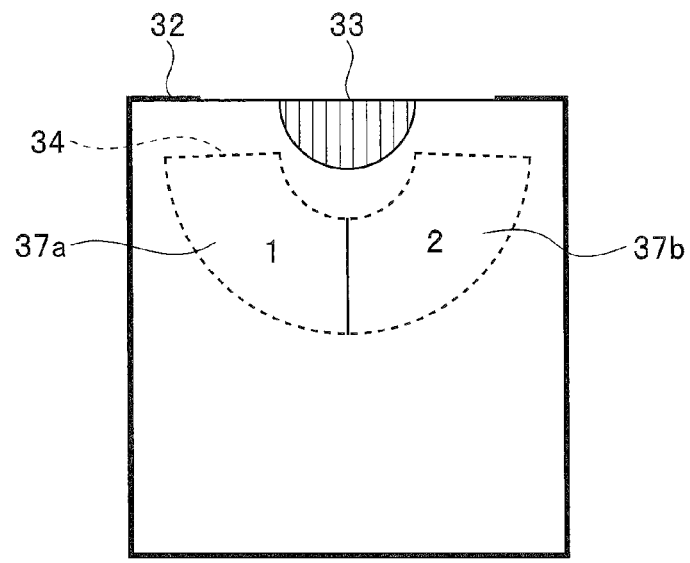
FIG. 10 is a diagram showing a first division example in dividing the proper-image determination region by a variable value in the ROI of the first embodiment.
Figure 11:
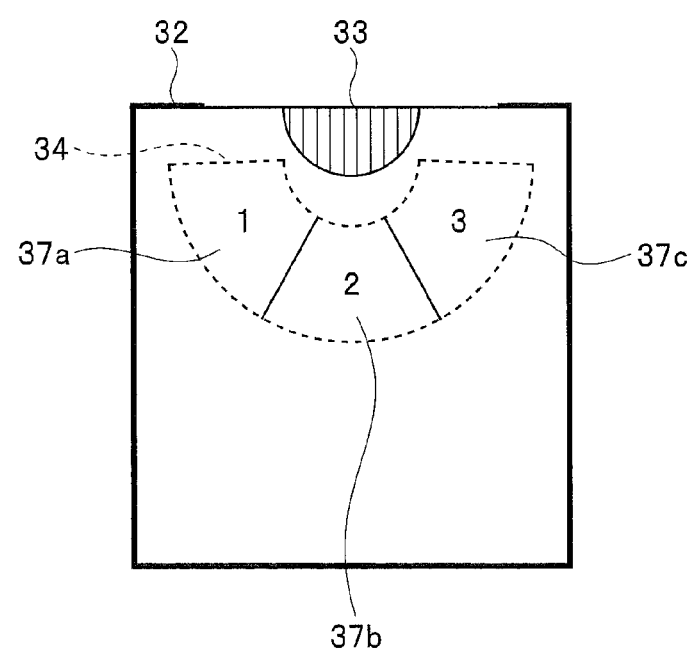
FIG. 11 is a diagram showing a second division example in dividing the proper-image determination region by a variable value in the ROI of the first embodiment.
Figure 12:
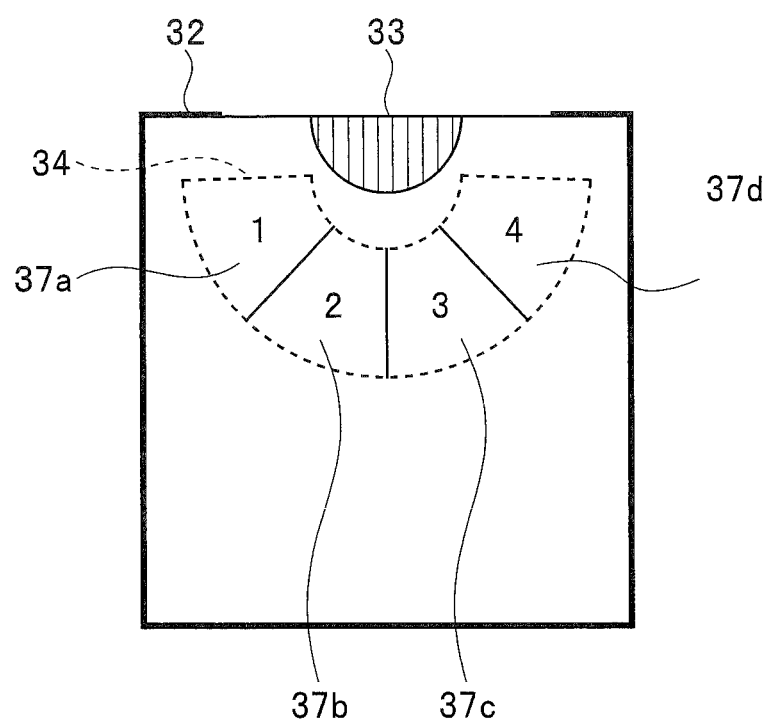
FIG. 12 is a diagram showing a third division example in dividing the proper-image determination region by a variable value in the ROI of the first embodiment.

Consequently, as shown in FIG. 10 to FIG. 12, variable-value division is performed in which the number of the proper-image determination regions 37 sequentially increases to two (37a and 37b) shown in FIG. 10, three (37a to 37c) shown in FIG. 11, and four (37a to 37d) shown in FIG. 12. FIG. 10 is a diagram showing a first division example in dividing the proper-image determination region 37 by a variable value in the ROI 34. FIG. 11 is a diagram showing a second division example in dividing the proper-image determination region 37 by a variable value in the ROI 34. FIG. 12 is a diagram showing a third division example in dividing the proper-image determination region 37 by a variable value in the ROI 34.

When it is determined in step S60 that n is larger than the upper limit value nf or it is determined in step S56 that the processing target elastic image is a proper image, the ultrasound observation apparatus returns from this processing to the processing shown in FIG. 13.

Note that the number of divisions n is changed from the lower limit value ni to the upper limit value nf. However, the number of divisions n may be changed from the upper limit value nf to the lower limit value ni. The change of the number of divisions n is not limited to these examples. The number of divisions n may be changed in appropriate order between a value equal to or larger than the lower limit value ni and a value equal to or smaller than the upper limit value nf.

Note that (1) the threshold compared with the size of the ROI 34 in step S4 of FIG. 13, (2) the angle of the proper-image determination region 37 in step S31 and the offset amount in step S35 of FIG. 15, (3) the fixed value in step S41 of FIG. 16, and (4) the lower limit value ni in step S51 and the upper limit value nf in step S60 of FIG. 17 may be automatically set based on design values or a user may manually set the values. In this case, concerning (2), (3), and (4), the determination-region setting section 25, the proper-image determining section 27, or the like may store, in advance, a table for giving predetermined values corresponding to the size of the center angle of the ROI 34. The ultrasound observation apparatus may determine the respective values referring to the table based on the size of the center angle of the ROI 34 set by the user or the like.

In the above explanation, which processing of the single region processing in step S5, the sequential scan of step S7, the fixed-value division of step S9, and the variable-value division of step S10 is performed is automatically set. However, the user may manually select the processing.

Further, in the respective kinds of processing explained above, when it is determined that the proper-image determination region 37 is a proper region, the proper-image determining section 27 may further superimposes a region determined as a proper region on the elastic image, cause the image display section 31 to display the region, and clearly indicate the region to the user. In this case, the proper-image determining section 27 generates a signal for superimposing and displaying the proper-image determination region 37 determined as proper on the elastic image and transmits the signal to the image display section 31.

In the above explanation, the intra-body cavity probe 2 is explained as an example. However, the present invention is not limited to this. The ultrasound probe may be an external ultrasound probe. When the ultrasound probe is the external ultrasound probe, specifically, a linear ultrasound probe, the threshold compared with the size of the ROI 34 in step S4 of FIG. 13 only has to be, for example, length in a linear scan direction.

According to such a first embodiment, the proper-image determination region 37 is set according to the size of the ROI 34. It is determined based on the region characteristic of the proper-image determination region 37 whether the elastic image is a proper image. Therefore, it is possible to automatically extract a proper image without depending on the size of the ROI 34.

When the size of the ROI 34 is equal to or smaller than the threshold, the entire ROI 34 is set as the proper-image determination region 37. When the size of the ROI 34 is larger than the threshold, the partial region is set as the proper-image determination region 37. Therefore, it is possible to perform appropriate determination according to the size of the displacement source 36.

Further, when the sequential scan is performed, it is possible to perform appropriate determination without depending on the position of the displacement source 36 with respect to the ROI 34.

When the fixed-value division is performed, it is possible to perform appropriate determination not depending on the position of the displacement source 36 without requiring the processing for moving the proper-image determination region 37.

On the other hand, when the variable-value division is performed, it is possible to cope with a change in a size of a region that receives pressure from the displacement source 36.

When at least one of the average, the dispersion, and the deviation of the displacement and the average, the dispersion, and the deviation of the elasticity information of the proper-image determination region 37 is calculated as the region characteristic, it is possible to perform appropriate determination corresponding to the displacement or the elasticity information.

Further, when at least one of the number of colored pixels and the total area of the colored pixels of the proper-image determination region 37, the ratio of the number of colored pixels to the number of pixels of the entire proper-image determination region 37, and the ratio of the total area of the colored pixels to the area of the entire proper-image determination region 37 is calculated as the region characteristic, it is possible to perform appropriate determination using the colored pixels.

When at least one of the average of the pressure, the rate of change of the pressure, the dispersion of the pressure, and the deviation of the pressure of the proper-image determination region 37 is calculated as the region characteristic, it is possible to perform appropriate determination corresponding to the pressure.

In addition, the proper-image determination region 37 determined as proper is superimposed and displayed on the elastic image. Therefore, the user can easily check the proper-image determination region 37, based on which the elastic image is determined as the proper image.

Note that, in the above explanation, the ultrasound observation system including the ultrasound observation apparatus is mainly explained. However, the present invention may be an actuation method for actuating the ultrasound observation apparatus or the ultrasound observation system as explained above, a processing program for causing a computer to actuate the ultrasound observation apparatus or the ultrasound observation system as explained above, a non-transitory recording medium that records the processing program and is readable by the computer, and the like.

The present invention is not limited to the embodiment per se. In an implementation stage, the constituent elements can be modified and embodied in a range not departing from the spirit of the present invention. Forms of various inventions can be formed by appropriate combinations of the plurality of constituent elements disclosed in the embodiment. For example, several constituent elements can be deleted from all the constituent elements described in the embodiments. Further, the constituent elements described in different embodiments may be combined as appropriate. In this way, it goes without saying that various modifications and applications are possible in a range not departing from the spirit of the invention.

What is claimed is:

1. An ultrasound observation apparatus that generates an ultrasound image based on an ultrasound signal generated from ultrasound transmitted to a subject and reflected, the ultrasound observation apparatus comprising:
a computer configured to:
transmit a driving signal for generating the ultrasound transmitted to the subject;
receive the ultrasound signal generated from the ultrasound reflected by the subject;
measure displacement of the subject based on the ultrasound signal received;
generate one or more elastic images based on the displacement measured;
control a memory to store the one or more elastic images generated;
compare a size of a region of interest (ROI) in an elastic image of the one or more elastic images, with a threshold;
in a first case where the size of the ROI is equal to or smaller than the threshold, set an entirety of the ROI as a proper-image determination region;
in a second case where the size of the ROI is larger than the threshold, set one or more partial regions, where each of the one or more partial regions is a part of the ROI, as the proper-image determination region,
wherein the proper-image determination region is a region for determining a proper image suitable for diagnosis and storage of the proper image out of the one or more elastic images stored in the memory;
calculate a region characteristic of the proper-image determination region based on the displacement measured or on elasticity information of the elastic images generated; and
determine based on the region characteristic calculated whether the elastic image in which the proper-image determination region is set is the proper image or not.

2. The ultrasound observation apparatus according to claim 1,
wherein, in the second case, the one or more partial regions is a plurality of partial regions, and the computer is configured to set the plurality of partial regions at different positions such that the entirety of the ROI is covered with the plurality of partial regions in all of the positions and sequentially set each of the set plurality of partial regions as the proper-image determination region.

3. The ultrasound observation apparatus according to claim 1,
wherein, in the second case, the one or more partial regions is a plurality of partial regions, and the computer is configured to divide the entirety of the ROI into the plurality of partial regions and sequentially set the plurality of partial regions as the proper-image determination region.

4. The ultrasound observation apparatus according to claim 3,
wherein a number of the divided partial regions is set based on a fixed value.

5. The ultrasound observation apparatus according to claim 3,
wherein the computer is configured to change a number of the divided partial regions between a value equal to or larger than a lower limit value and a value equal to or smaller than an upper limit value until the proper-image determination region determined as proper is found.

6. The ultrasound observation apparatus according to claim 1,
wherein the computer is configured to determine based on the region characteristic whether the proper-image determination region is proper or not and, when determination that the proper-image determination region is proper is made for at least one of one or more proper-image determination regions set from the one or more partial regions, determine that the elastic image in which the proper-image determination region is set is a proper image.

7. The ultrasound observation apparatus according to claim 1,
wherein the computer is configured to calculate, as the region characteristic, at least one of an average of the displacement of the proper-image determination region measured, dispersion of the displacement, and a deviation of the displacement and an average of the elasticity information of the proper-image determination region calculated, dispersion of the elasticity information, and a deviation of the elasticity information.

8. The ultrasound observation apparatus according to claim 1,
wherein the computer is configured to calculate a distortion amount of the ROI based on displacement measured and perform coloring on pixels of the elastic image, the distortion amount of which is equal to or larger than a predetermined value, and wherein the computer is configured to calculate, as the region characteristic, at least one of a number of the colored pixels and a total area of the colored pixels of the proper-image determination region, a ratio of the number of colored pixels to a number of pixels of the entire proper-image determination region, and a ratio of a total area of the colored pixels to an entire area of the proper-image determination region.

9. The ultrasound observation apparatus according to claim 1,
wherein the computer is configured to generate a signal for displaying the proper-image determination region determined as proper on the elastic image.

10. An ultrasound observation system comprising:
the ultrasound observation apparatus according to claim 1; and
an ultrasound probe configured to:
receive the driving signal transmitted;
transmit the ultrasound to the subject;
receive the ultrasound reflected by the subject;
generate the ultrasound signal; and
transmit the ultrasound signal to the ultrasound observation apparatus.

11. The ultrasound observation system according to claim 10,
wherein the ultrasound probe further comprises a pressure detecting sensor configured to detect pressure on an ultrasound transmission/reception surface for transmitting and receiving the ultrasound, and
wherein the computer is configured to calculate, as the region characteristic, at least one of an average of pressure, a rate of change of the pressure, dispersion of the pressure, and a deviation of the pressure of the proper-image determination region obtained based on a detection result of the pressure detecting sensor.

12. An actuation method for an ultrasound observation apparatus that generates an ultrasound image based on an ultrasound signal generated from ultrasound transmitted to a subject and reflected, the actuation method comprising:
a step in which a computer transmits a driving signal for generating the ultrasound transmitted to the subject;
a step in which the computer receives the ultrasound signal generated from the ultrasound reflected by the subject;
a step in which the computer measures displacement of the subject based on the ultrasound signal received;
a step in which the computer generates one or more elastic images based on the displacement measured;
a step in which the computer controls a memory to store the one or more elastic images generated;
a step in which the computer compares a size of a region of interest (ROI) in an elastic image of the one or more elastic images, with a threshold;
a step in which, in a first case where the size of the ROI is equal to or smaller than the threshold, the computer sets an entirety of the ROI as a proper-image determination region;
a step in which, in a second case where the size of the ROI is larger than the threshold, the computer sets one or more partial regions, where each of the one or more partial regions is a part of the ROI, as the proper-image determination region,
wherein the proper-image determination region is a region for determining a proper image suitable for diagnosis and storage of the proper image out of the one or more elastic images stored in the memory;
a step in which the computer calculates a region characteristic of the proper-image determination image based on the displacement measured or elasticity information of the elastic images generated; and
a step in which the computer determines based on the region characteristic whether the elastic image in which the proper-image determination region is set is the proper image or not.

* * * * *